United States Patent
Winn et al.

(10) Patent No.: US 11,273,120 B2
(45) Date of Patent: Mar. 15, 2022

(54) HAIR TREATMENTS

(71) Applicant: Actera Ingredients, Inc., Newtown, PA (US)

(72) Inventors: Daniel Winn, Kingston, NJ (US); Lorraine Lampe, Philadelphia, PA (US)

(73) Assignee: Actera Ingredients, Inc., Newtown, PA (US)

( * ) Notice: Subject to any disclaimer, the term of this patent is extended or adjusted under 35 U.S.C. 154(b) by 0 days.

(21) Appl. No.: 16/687,337

(22) Filed: Nov. 18, 2019

(65) Prior Publication Data

US 2021/0145729 A1 May 20, 2021

(51) Int. Cl.
| | |
|---|---|
| *A61K 8/9728* | (2017.01) |
| *A61K 8/41* | (2006.01) |
| *A61Q 5/00* | (2006.01) |

(52) U.S. Cl.
CPC ............ *A61K 8/9728* (2017.08); *A61K 8/415* (2013.01); *A61Q 5/00* (2013.01); *A61K 2800/805* (2013.01); *A61K 2800/85* (2013.01)

(58) Field of Classification Search
CPC .................. A61K 8/9728; A61K 8/415; A61K 2800/805; A61K 2800/85; A61Q 5/00
See application file for complete search history.

(56) References Cited

U.S. PATENT DOCUMENTS

| | | | |
|---|---|---|---|
| 3,472,243 A | 10/1969 | Wall et al. | |
| 3,634,022 A | 1/1972 | Robbins et al. | |
| 5,457,040 A * | 10/1995 | Jarry | C12P 7/44 435/142 |
| 7,531,008 B2 | 5/2009 | Lagrange | |
| 8,668,745 B2 | 3/2014 | Gross et al. | |
| 9,498,419 B2 | 11/2016 | Pressly et al. | |
| 2005/0139119 A1* | 6/2005 | Rader | C09G 1/02 106/3 |
| 2005/0215060 A1* | 9/2005 | Oh | H01L 21/3212 438/692 |
| 2015/0313816 A1 | 11/2015 | Daubresse | |
| 2016/0296449 A1 | 10/2016 | Kadir et al. | |
| 2017/0340553 A1 | 11/2017 | Anderheggen et al. | |
| 2018/0055750 A1 | 3/2018 | Flohr et al. | |
| 2018/0369099 A1 | 12/2018 | Kita-Tokarczyk et al. | |
| 2019/0192398 A1 | 6/2019 | Wagner | |
| 2019/0201308 A1 | 7/2019 | Flohr | |
| 2020/0188246 A1* | 6/2020 | Gebert-Schwarzwaelder | A61K 8/23 |

FOREIGN PATENT DOCUMENTS

| | | | | |
|---|---|---|---|---|
| DE | 202016000077 U1 * | 12/2016 | .......... | A61K 8/9789 |
| WO | 2000071658 A1 | 11/2000 | | |
| WO | 2017197931 A1 | 11/2017 | | |
| WO | 2018039290 A1 | 3/2018 | | |
| WO | 2018039328 A1 | 3/2018 | | |
| WO | WO-2018174572 A1 * | 9/2018 | .............. | C09J 11/00 |
| WO | WO-2019001856 A1 * | 1/2019 | .............. | A61K 8/365 |
| WO | 2020264257 A1 | 12/2020 | | |

* cited by examiner

*Primary Examiner* — Ali Soroush

(74) *Attorney, Agent, or Firm* — Stinson LLP

(57) ABSTRACT

Various compositions and methods for treating or preventing damage to hair, especially in over-processed or chemically treated hair, are described.

23 Claims, No Drawings

HAIR TREATMENTS

FIELD OF THE INVENTION

The present invention relates to various compositions and methods for treating or preventing damage to hair, especially in over-processed or chemically treated hair.

BACKGROUND OF THE INVENTION

Human hair is frequently subjected to chemical processes that damage the structural integrity of the hair fiber. Hair is formed from layers of keratin protein which are polymeric, as well as the natural pigments that provide the inherent natural hair color. Due to various beauty and fashion trends, as well as the desire to avoid grey hair, consumers frequently subject their hair to harsh chemical processes such as application of chemicals that are highly reactive and initiate the breaking of intramolecular bonds within keratin, or the destruction of melanin, or both. Popular beauty treatments that involve chemical hair processes including oxidation hair lightening and oxidative hair coloring, during which oxidizing agents such as peroxides, persulfates, and oxidizing enzymes are applied to the hair. Other popular beauty treatments that involve chemical processes are permanent waves and hair relaxers and straighteners, which involve the application of reducing agents such as formaldehyde, lye, and thiol reducing agents such as thioglycolates. These beauty treatments are referred to interchangeably as chemical processes or chemical treatments.

Because hair constantly grows, new hair growth must be treated to match previously treated hair. Therefore, chemical treatments are often performed several times per year, year after year. Hair that repeatedly undergoes chemical treatments is referred to as over-processed or damaged hair.

Hair damage occurs in a number of ways. The oxidizing and reducing agents react with and damage the cuticle which is the exterior layer of dead cells and proteins protecting the cortex of keratin in the hair fiber. The degraded cuticle results in more penetration of oxidizing or reducing chemicals. The damaged cuticle also results in daily assault from environmental UV light, ozone, and moisture all of which further compromise the structural integrity of the hair fiber. Chemical processes also degrade melanin, creating voids in the hair fiber where moisture can diffuse into. Hair fibers, once damaged and with more voids, permit greater diffusion of materials into and out of the hair. Chemical treatment agents penetrate further into the cortex where they react with keratin protein fibrils. Intramolecular keratin bonds are broken, and the keratin proteins degrade into low molecular weight keratin peptide fragments, which are more water soluble. With repeated hair washing the peptide fragments are washed away creating even more porous hair. Over-processed hair becomes increasingly porous with less keratin content compared to virgin untreated hair, has weakened intramolecular bonds, is mechanically compromised, and easily breaks.

Standard treatment for ameliorating the condition of over-processed hair is to apply topical hair conditioners to the hair on a regular basis. Hair conditioners are products that use hydrophobic fluids, oils, and cationic surfactants to coat the exterior of hair fibers to improve the surface and visual characteristics of the hair.

Other solutions to treat over-processed hair have been suggested. For example, U.S. Pat. No. 3,472,243 describes applying to damaged hair vinyl monomers, along with oxidizing agents to polymerize the monomer inside the hair fiber. Also, U.S. Pat. No. 3,634,022 describes applying olefinicaly unsaturated polymerizable monomers and an effective amount of a peroxide initiator to hair to yield improved hair setting and hair conditioning benefits.

However, these solutions suffer from several disadvantages. One disadvantage of these compositions and methods is that the in situ polymerization of vinyl monomers produces only polyvinyl polymers, such as polyacrylates. Polyvinyl polymers are stiff fixatives commonly used in coatings and hair sprays. Hair treated with such compositions are stiff and lack the natural bounce and flow of virgin human hair. Furthermore, polyvinyl polymers have only a carbon-carbon backbone, unlike natural keratin which consists of many amide bonds. The existence of polyvinyl polymers inside of hair creates different attractive and repulsive forces compared to the native proteins of hair. Thus, when hair dyes are applied, the hair may not retain the dye in the same manner as natural keratin fibrils.

Thus, there remains a need for compositions and methods to repair the hair fiber from the inside, to fill voids within fibers, to reduce the porosity of the hair fiber, and to increase the hydrophobicity and strength of fibers within the internal hair cortex. By strengthening the internal cortex, hair can withstand repeated chemical oxidation and reduction treatments and maintain structural integrity of the hair fibers.

BRIEF SUMMARY OF THE INVENTION

Various aspects of the present invention are directed to compositions for treating hair (e.g., damaged hair, over-processed hair, and/or chemically treated hair). In various embodiments, the compositions comprise (a) *Aspergillus terreus* fermentation product or a fraction or an isolate thereof and (b) a basic amino acid and/or an amino alcohol.

Further aspects of the present invention are directed to kits for treating hair. In various embodiments, the kits comprise a first component comprising *Aspergillus terreus* fermentation product or a fraction or an isolate thereof; a second component comprising the basic amino acid and/or amino alcohol; and a hair chemical component comprising an oxidizing agent or precursor thereof.

Other aspects of the present invention are directed to methods of treating hair fibers. In some embodiments, the methods comprise contacting the hair fibers with a composition comprising *Aspergillus terreus* fermentation product or a fraction or an isolate thereof and a basic amino acid and/or amino alcohol and then exposing the hair fibers to an oxidizing agent. In further embodiments, the methods comprise contacting the hair fibers with a composition comprising an *Aspergillus terreus* fermentation product or a fraction or an isolate thereof and a basic amino acid and/or amino alcohol and an oxidizing agent.

Still further aspects are directed to processes for preparing various compositions as described herein. In various embodiments, the processes comprise combining (a) an *Aspergillus terreus* fermentation product or a fraction or an isolate thereof and (b) a basic amino acid and/or amino alcohol.

Other objects and features will be in part apparent and in part pointed out hereinafter.

DETAILED DESCRIPTION OF THE INVENTION

In general, the present invention is directed to compositions and methods for treating hair and methods of producing these compositions. In particular, various aspects relate to compositions and methods for treating or preventing damage to hair, especially in over-processed or chemically treated hair. Applicants have surprisingly discovered that fermentation products or a fraction or an isolate thereof of *Aspergillus terreus* can be applied to hair and can react oxidatively, without the need of a bridging agent, to form compositions in situ that provide an improved ability to repair, strengthen and retain dye in the hair. Accordingly, various compositions provided herein comprise (a) an *Aspergillus terreus* fermentation product or a fraction or an isolate thereof and (b) a basic amino acid and/or an amino alcohol. Various methods for treating hair fibers comprise contacting the hair fibers with (a) an *Aspergillus terreus* fermentation product or a fraction or an isolate thereof, (b) a basic amino acid and/or amino alcohol, (c) an oxidizing agent, or any mixture comprising two or more of these ingredients. Additional embodiments are described herein.

Compositions

As noted, various aspects of the present invention are directed to compositions for treating hair or hair fibers. In various embodiments, the compositions comprise at least two different components. For instance, the first component can be an *Aspergillus terreus* fermentation product or a fraction or an isolate thereof and the second component can comprise an amino acid and/or amino alcohol. Accordingly, in some embodiments, the composition comprises (a) an *Aspergillus terreus* fermentation product or a fraction or an isolate thereof and (b) a basic amino acid and/or an amino alcohol.

*Aspergillus terreus* are filamentous fungi and are known to produce numerous useful metabolites such as polyketides, including statin drugs widely used for the treatment of high blood pressure, as well as organic acids, lactones, enzymes, and secondary metabolites such as territrem A, citreoviridin, citrinin, gliotoxin, patulin, terrein, terreic acid, and terretonin. Naturally occurring *Aspergillus terrerus* may produce all or some of these metabolites from simple carbohydrate sources such as glucose or other sugars during fermentation. The fermentation temperature for producing the fermentation broth is typically between 20° C. and 70° C., with a preferred temperature of 40° C.

In various embodiments, the fermentation product or a fraction or an isolate thereof of *Aspergillus terreus* comprises an aqueous fermentation broth. The broth can be separated from the fermentation biomass, be free of particulates, and contain only soluble organic compounds produced by the fermentation and optionally soluble residual substrate ingredients such as sugar should there be any remaining in the broth. In various embodiments, the fermentation product or a fraction or an isolate thereof can be aqueous or it can be post processed to remove water, for example by drying, to yield a powdered organic solid (e.g., an anhydrous fermentation product or a "dried fermentation broth") that can be rehydrated into an aqueous solution prior to application to hair in the hair repair process.

In various embodiments, the composition has a concentration of the *Aspergillus terreus* fermentation product or a fraction or an isolate thereof that is about 0.1 wt. % or greater, about 1 wt. % or greater, about 2 wt. % or greater, about 5 wt. % or greater, about 10 wt. % or greater, or about 20 wt. % or greater. For example, in some embodiments, the composition can have a concentration of *Aspergillus terreus* fermentation product or a fraction or an isolate thereof that is from about 0.1 wt. % to about 20 wt. %, from about 0.1 wt. % to about 10 wt. %, from about 0.1 wt. % to about 7.5 wt. %, from about 0.1 wt. % to about 5 wt. %, from about 0.1 wt. % to about 2.5 wt. %, from about 1 wt. % to about 20 wt. %, from about 1 wt. % to about 10 wt. %, from about 1 wt. % to about 7.5 wt. %, from about 1 wt. % to about 5 wt. %, or from about 1 wt. % to about 2.5 wt. %.

Further, in various embodiments, the composition has a concentration of the basic amino acid and/or amino alcohol that is about 0.5 wt. % or greater, about 1 wt. % or greater, about 2 wt. % or greater, about 5 wt. % or greater, about 10 wt. % or greater, or about 20 wt. % or greater. For example, in certain embodiments, the composition has a concentration of the basic amino acid and/or amino alcohol that is from about 0.5 wt. % to about 20 wt. %, from about 0.5 wt. % to about 15 wt. %, from about 0.5 wt. % to about 10 wt. %, from about 0.5 wt. % to about 7.5 wt. %, from about 1 wt. % to about 20 wt. %, from about 1 wt. % to about 15 wt. %, from about 1 wt. % to about 10 wt. %, from about 1 wt. % to about 7.5 wt. %, from about 5 wt. % to about 20 wt. %, from about 5 wt. % to about 15 wt. %, from about 5 wt. % to about 10 wt. %, or from about 5 wt. % to about 7.5 wt. %.

In some embodiments, the weight of basic amino acid and/or an amino alcohol in the composition is greater than the weight of the *Aspergillus terreus* fermentation product or a fraction or an isolate thereof. For example, the weight ratio of the basic amino acid and/or amino alcohol to the *Aspergillus terreus* fermentation product or a fraction or an isolate thereof can be about 1.5:1 or greater, about 2:1 or greater, about 3:1 or greater, about 4:1 or greater, about 5:1 or greater, about 10:1 or greater, or about 20:1 or greater. In these and other embodiments, the weight ratio of the basic amino acid and/or amino alcohol to the *Aspergillus terreus* fermentation product or a fraction or an isolate thereof is from about 1:1 to about 50:1, from about 3:1 to about 25:1, from about 1:1 to about 10:1, from about 1:1 to about 5:1, from about 1:1 to about 3:1, from about 3:1 to about 50:1, from about 3:1 to about 25:1, from about 3:1 to about 10:1, or from about 3:1 to about 5:1.

In further embodiments, the weight of the *Aspergillus terreus* fermentation product or a fraction or an isolate thereof in the composition is greater than the weight of the basic amino acid and/or an amino alcohol. For example, the weight ratio of the *Aspergillus terreus* fermentation product or a fraction or an isolate thereof to the basic amino acid and/or amino alcohol is about 1.5:1 or greater, about 2:1 or greater, about 3:1 or greater, about 4:1 or greater, about 5:1 or greater, about 10:1 or greater, or about 20:1 or greater. In these and other embodiments, the weight ratio *Aspergillus terreus* fermentation product or a fraction or an isolate thereof to the basic amino acid and/or amino alcohol is from about 1:1 to about 50:1, from about 3:1 to about 25:1, from about 1:1 to about 10:1, from about 1:1 to about 5:1, from about 1:1 to about 3:1, from about 3:1 to about 50:1, from about 3:1 to about 25:1, from about 3:1 to about 10:1, or from about 3:1 to about 5:1.

As noted, in various embodiments, the composition can comprise an *Aspergillus terreus* fermentation product or a fraction or an isolate thereof. In some embodiments, the *Aspergillus terreus* fermentation product or a fraction or an isolate thereof can be a liquid fermentation product (e.g., a fermentation broth). In some embodiments the *Aspergillus terreus* fermentation product or a fraction or an isolate thereof can comprise a dried or anhydrous *Aspergillus terreus* fermentation product (e.g., a dried or anhydrous fermentation broth powder).

As noted, the composition comprises a basic amino acid and/or an amino alcohol. In various embodiments, the composition comprises the basic amino acid. In some embodiments, the basic amino acid comprises arginine, lysine, and/or histidine. In certain embodiments, the basic amino acid comprises arginine and/or lysine. In various embodiments, the basic amino acid comprises or consists of arginine.

In various embodiments, the composition comprises the amino alcohol. In some embodiments, the amino alcohol comprises at least one alcohol selected from the group consisting of triethanolamine, diethanolamine, monoethanolamine, 2-amino-2-methyl-1-propanyl, and combinations thereof. In certain embodiments, the composition comprises a combination of the basic amino acid and amino alcohol.

*Aspergillus terreus* fermentation products or fractions or an isolates thereof (e.g., fermentation broths) are typically acidic. The basic amino acid and/or amino alcohol, accordingly, can serve to adjust the pH to a suitable level (i.e., less acidic).

In various embodiments, the compositions described herein can have a pH of about 7 or less, about 6.5 or less, about 6 or less, about 5.5 or less, about 5 or less, about 4.5 or less, about 4 or less, or about 3 or less. In some embodiments, the compositions described herein can have a pH of from about 3 to about 7, from about 3 to about 6, from about 3 to about 5, from about 3 to about 4, from about 4 to about 7, from about 4 to about 6, or from about 4 to about 5.

In various embodiments, the compositions described herein further comprise a solvent. For example, the solvent can comprises an aqueous solvent (e.g., water). When prepared as a solution, the total amount of (a) *Aspergillus terreus* fermentation product or a fraction or an isolate thereof and (b) basic amino acid, and/or amino alcohol in solution can be about 10 wt. % or less or from about 1 wt. % to about 10 wt. %. For example, when the solvent is water, the total concentration of (a) *Aspergillus terreus* fermentation product or a fraction or an isolate thereof and (b) basic amino acid, and/or amino alcohol can be less than about 10 wt. % or from about 1 wt. % to about 10 wt. %.

As noted, it has been discovered that the two or more components as described herein (e.g., the *Aspergillus terreus* fermentation product or a fraction or an isolate thereof and the amino acid and/or amino alcohol) can advantageously polymerize in situ to form flexible but strong polymers that can strengthen hair fibers and ameliorate hair damage due to chemical treatments. In various embodiments, an oxidizing agent is used to induce polymerization in the hair fibers. Accordingly, in some embodiments, the compositions described herein further comprise an oxidizing agent or precursor thereof. In certain embodiments, the oxidizing agent comprises a conventional chemical used in hair treatment formulations to change the color of the hair fibers.

In various embodiments, the oxidizing agent can comprise at least one chemical selected from the group consisting of hydrogen peroxide, urea peroxide, alkali metal bromates or ferricyanides, peroxygenated salts (e.g., persulfates, perborates, peracids and precursors thereof as well as percarbonates of alkali metals or alkaline earth metals) and combinations thereof. In some embodiments, the oxidizing agent comprises at least one chemical selected from the group consisting of hydrogen peroxide, persulfates, and combinations thereof. In various embodiments, the oxidizing agent is provided as a conventional or commercial hair treatment composition (e.g., a dyeing composition, bleaching paste, or other chemical treatment).

The compositions can be formulated in various suitable forms including, for example, low to moderate viscosity liquids, lotions, milks, mousses, sprays, gels, creams, shampoos, conditioners, and the like. In various embodiments, the compositions described herein are formulated as a hair conditioner or shampoo. Various compositions described herein can be applied to hair fibers prior to exposure of the hair fibers to the oxidizing agent.

The compositions described herein may further comprise one or more additives (e.g., cosmetically acceptable ingredients). Examples of cosmetically acceptable ingredients are those listed in the International Cosmetic Ingredient Dictionary and Handbook and those listed in the United States Pharmacopeia. Cosmetically acceptable ingredients include, but are not limited to preservatives, antioxidants, chelating agents, sunscreen agents, vitamins, dyes, hair coloring agents, proteins, amino acids, natural extracts such as plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, salts, pH adjusting agents (e.g., citric acid), neutralizing agents, buffers, hair conditioning agents, anti-static agents, anti-frizz agents, anti-dandruff agents, absorbents, and combinations thereof.

For example, surfactants include various anionic, cationic, nonionic, and amphoteric surfactants. Anionic surfactants include, but are not limited to, those containing carboxylate, sulfonate and sulfate ions. Examples of anionic surfactants include sodium, potassium, ammonium of long chain alkyl sulfonates and alkyl aryl sulfonates. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine. Emollients include, for example, silicone compounds, polyols (e.g., propanediol), and triglycerides Emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, polysorbate-80, and combinations thereof.

Preservatives include, but are not limited to, glycerin containing compounds, benzyl alcohol, parabens, sodium benzoate, ethylenediamine-tetraacetic acid (EDTA), potassium sorbate, and so on. Antioxidants include, for example, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

Conditioning agents include, for example, silicone-based agents, panthenol, hydrolyzed wheat and/or soy protein, amino acids, rice bran wax, meadowfoam seed oil, mango seed oil, grape seed oil, jojoba seed oil, sweet almond oil, hydroxyethyl behenamidopropyl diimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

Viscosity modifying agents include, for example, viscous liquids, such as polyethylene glycol, semisynthetic polymers, cellulose derivatives, synthetic polymers, naturally occurring polymers, bentonite, colloidal silicon dioxide, and microcrystalline cellulose, and salts, such as sodium chloride, and combinations thereof.

Opacifying agents include, but are not limited to, glycol distearate and ethoxylated fatty alcohols.

In some embodiments, the compositions described herein comprise at least one of a viscosity modifier (e.g., xanthan gum or equivalent), a preservative (e.g., phenoxyethanol), an emollient (e.g., propanediol), a conditioning agent (e.g., stearamidopropyl dimethylamine, behentrimonium methosulfate, and/or sunflower oil), or an emulsifier (e.g., cetearyl alcohol). In certain embodiments, the composition comprises an *Aspergillus terreus* fermentation product or a fraction or an isolate thereof, arginine, cetearyl alcohol, behentrimonium methosulfate, stearamidopropyl dimethylamine, sunflower oil, xanthan gum, propanediol, and phenoxyethanol.

Kits

Various aspects of the present invention also include kits for treating hair. In various embodiments, a kit for treating hair comprises: a first component comprising an *Aspergillus terreus* fermentation product or a fraction or an isolate thereof; a second component comprising the basic amino acid and/or amino alcohol; and a hair chemical component comprising an oxidizing agent or precursor thereof. The amount of the oxidizing agent in the hair chemical component is sufficient to effectively polymerize the first and second components to provide the intended protective/repairing effects.

Features relating to the compositions described herein can apply to any of the components of the kits. For example, the oxidizing agent can comprise at least one chemical selected from the group consisting of hydrogen peroxide, urea peroxide, alkali metal bromates, ferricyanides, peroxygenated salts, persulfates, and combinations thereof. Also, the components of the kit can include additives as described herein.

In some embodiments, the first component and the second component are present as a premixed composition. In certain embodiments, the premixed composition is a composition as described herein.

In other embodiments, the first component and the second component are separate compositions (e.g., in separate packaging or containers within the kit).

In various embodiments the kit contains more than one container (or more than one compartment in a given container) to avoid mixing of the oxidizing agent or precursor thereof with the components before use.

The kit may further include a developer bottle, gloves, shampoo, and/or conditioner. Instructions for use of the kit can also be included.

Method of Use

Further aspects of the present invention are directed to methods for treating hair fibers. In general, the methods comprise contacting hair fibers with a composition as described herein. As detailed below, the compositions described herein that comprise (a) the *Aspergillus terreus* fermentation product or a fraction or an isolate thereof and (b) the amino acid and/or amino alcohol may be applied to hair fibers before, simultaneously with, and/or after application of an oxidizing agent. When the compositions are applied simultaneously with the oxidizing agent, they may be applied as a single formulation (e.g., comprising the *Aspergillus terreus* fermentation product or a fraction or an isolate thereof, an amino acid and/or amino alcohol, and the oxidizing agent).

In various embodiments, the methods comprise contacting hair fibers with a composition comprising (a) the *Aspergillus terreus* fermentation product or a fraction or an isolate thereof and (b) the amino acid and/or amino alcohol as described herein and exposing the hair fibers treated with the composition to an oxidizing agent (e.g., contacting the hair fibers to an oxidizing agent). In some embodiments, the methods comprise contacting hair fibers with a hair treatment composition comprising (a) the *Aspergillus terreus* fermentation product or a fraction or an isolate thereof and (b) the amino acid and/or amino alcohol, and (c) an oxidizing agent (e.g., a premixed composition of (a), (b), and (c)).

It is believed that the fermentation product or a fraction or an isolate thereof of *Aspergillus terreus* can comprise various polymerizable functional groups which, in combination with the amino acid and/or amino alcohol in the compositions described herein, can react in the presence of the oxidizing agent to form a co-polymer. Ideally, this reaction can occur within or inside a hair fiber. For example, within a hair fiber, keratin polymers can act as a molecular sieve, forming a catalytic environment where many possible reaction structures are possible, including polyolefinic structures, polyesters, polyamides, polyester-amides, and copolymers thereof. There may be a distribution of various permutations of the polymer structures.

In various embodiments, the hair fibers are contacted with compositions comprising the *Aspergillus terreus* fermentation product or a fraction or an isolate thereof and an amino acid and/or amino alcohol before exposing the hair to an oxidizing agent.

As noted herein, in various embodiments, the oxidizing agent can comprise hydrogen peroxide, urea peroxide, alkali metal bromates or ferricyanides, peroxygenated salts (e.g., persulfates, perborates, peracids, and precursors thereof and percarbonates of alkali metals or of alkaline-earth metals). In some embodiments, the oxidizing agent is provided in a hair treatment formulation comprising a dye, a bleaching composition, or other oxidizing hair treatment components.

In other embodiments, the oxidizing agent can be UV light (e.g., sunlight). For example, in various embodiments, the methods can comprise contacting the hair fibers with a composition comprising an *Aspergillus terreus* fermentation product or a fraction or an isolate thereof and a basic amino acid and/or amino alcohol, as described above, and then exposing the hair fibers to UV light. In other embodiments, the hair fibers might be pre-treated with the composition comprising an *Aspergillus terreus* fermentation product or a fraction or an isolate thereof and a basic amino acid and/or amino alcohol prior to a hair treatment procedure (e.g., bleaching, dyeing, relaxing). Any of the compositions described above can be used in these methods.

In various embodiments, the compositions are aqueous compositions and may be applied to the hair by any means suitable (e.g., spraying, dripping, drenching etc.). In some embodiments, the compositions are incorporated into a hair conditioning product and applied to the hair before, during and/or following exposure to the oxidizing agent.

In various embodiments, the *Aspergillus terreus* fermentation product or a fraction or an isolate thereof and the basic amino acid and/or amino alcohol can be added to a water phase of a hair conditioner emulsion. The hair conditioning emulsion may further comprise one or more additives as described above.

As noted, in various embodiments, the methods comprise contacting hair fibers with a hair treatment composition comprising (a) the *Aspergillus terreus* fermentation product or a fraction or an isolate thereof and (b) the amino acid and/or amino alcohol, and (c) an oxidizing agent (e.g., a premixed composition of (a), (b), and (c)). In some embodiments, these methods further comprise combining the oxidizing agent with the composition comprising (a) the *Aspergillus terreus* fermentation product or a fraction or an isolate thereof and (b) the amino acid and/or amino alcohol to form the hair treatment composition. For example, an oxidizing agent (e.g., hydrogen peroxide, persulfate or equivalent) can be combined with a composition comprising the *Aspergillus terreus* fermentation product or a fraction or an isolate thereof and an amino acid and/or amino alcohol as described above to form the hair treatment composition. These hair treatment compositions can be applied to the hair within a relatively short period after forming the compositions. For example, the hair treatment compositions can be applied to the hair fibers within about 2 hours, within about 1 hour, within about 30 minutes, within about 20 minutes, within about 10 minutes, or within about 5 minutes of forming the hair treatment composition.

In various embodiments described herein, the methods of treating hair can further comprise exposing the hair fibers to UV light.

The compositions and methods described herein can have beneficial and restorative properties for hair fibers. Accordingly, in various embodiments, the methods of treating hair fibers described herein can comprise protecting or mitigating damage induced by the oxidizing agent. In some embodiments, the methods of treating hair fibers can comprise repairing damage to the hair fibers. In various embodiments, the methods of treating hair fibers can comprise increasing hydrophobicity, decreasing porosity, and/or increasing dye retention of the hair fibers. In certain embodiments, the methods of treating hair fibers can also comprise chemically treating the hair fibers. For example, the methods of treating can comprise bleaching, dyeing or relaxing the hair fibers.

In various embodiments, the methods comprise combining a composition as described herein with a bleaching compound to form a bleaching composition and contacting the hair fibers with the bleaching composition. In some embodiments, the methods comprise combining a composition as described herein with an oxidative hair dye to form a dyeing composition and contacting the hair fibers with the dyeing composition. In certain embodiments, the methods comprise combining a composition as described herein with a hair relaxing agent to form a hair relaxing composition and contacting the hair fibers with the hair relaxing composition.

In certain embodiments, the methods described herein can comprise contacting the hair fibers with an *Aspergillus terreus* fermentation product or a fraction or an isolate thereof and arginine.

Processes of Preparing the Compositions

Still further aspects are directed to processes for preparing various compositions described herein. In various embodiments, the processes comprise combining (a) an *Aspergillus terreus* fermentation product or a fraction or an isolate thereof and (b) a basic amino acid and/or amino alcohol. The processes can further comprise combining one or more other ingredients as described herein with a) an *Aspergillus terreus* fermentation product or a fraction or an isolate thereof, (b) a basic amino acid and/or amino alcohol, or any mixture thereof.

All percentages are by weight of the total composition unless specifically stated otherwise. When more than one composition is used during a treatment, the total weight to be considered is the total weight of all the compositions applied on hair simultaneously (i.e. the weight found "on head") unless otherwise specified. All ratios are weight ratios unless specifically stated otherwise.

As used herein the terms "hair" and "hair fibers" to be treated may be "living" (i.e., on a living body) or may be "non-living" (i.e., in a wig, hairpiece or other aggregation of non-living keratinous fibers). Mammalian hair, particularly human hair is preferred. However wool, fur and other keratin containing fibers are suitable substrates for the compositions according to the present invention.

Having described the invention in detail, it will be apparent that modifications and variations are possible without departing from the scope of the invention defined in the appended claims.

EXAMPLES

The following non-limiting examples are provided to further illustrate the present invention.

Example 1: Treating Over-Processed Bleached Hair

Over-processed hair was created by subjecting virgin human black hair tresses to repeated bleaching with a conventional salon bleaching system: a 40 volume developer (hydrogen peroxide) and a persulfate oxidizing powder manufactured by L'Oreal. The bleaching treatment was applied following the manufacturer's instructions and was repeated four times, each time for two hours, until all natural black melanin pigment was oxidized to a blond color and the hair fibers were noticeably damaged. The over-processed hair tresses were subjected to a final hair bleaching process per the manufacturer's instructions.

For Tress 1, 10 ml of aqueous test composition was added to the bleaching paste immediately prior to application on the hair. The aqueous test composition was clear aqueous solution containing 8.5% by weight of organic solids with a pH of 3.5, and was formulated by mixing 6.5 grams of dried anhydrous *Aspergillus terreus* fermentation product, 2 grams of arginine, and 91.5 grams of water to produce 100 grams of solution.

For Tress 2, the final bleaching was performed without any hair repair solution.

After the final bleaching and drying of the hair tresses, an expert hair technician combed each tress 10 times. The technician's evaluation is reported in Table 1. Tress 1 with the test composition was smooth and shiny, with all fibers aligning with each other with little breakage. Tress 2, with no repair solution, exhibited frizz with many hairs having lost their natural curl. Tress 2 was also significantly more damaged. Combing Tress 2 resulted in significant breakage.

TABLE 1

| Test Parameter | Tress 1 | Tress 2 |
| --- | --- | --- |
| Ease of Combing | 9/10 | 2/10 |
| Breakage Post Combing | None | Yes |
| Natural Fiber Wave | 7/10 | 1/10 |
| Visibly Smooth | Yes | No |

Example 2: Increased Hydrophobicity and Faster Drying

Tress 1 and Tress 2 obtained from Example 1 were wetted with equal quantities of distilled water and immediately hung to air dry. After 1 hour, the tresses were weighed to determine the amount of water remaining in the fibers. Tress 1, which had previously been treated with the test composition, had 50% of its water remaining in it. Tress 2, which had not been treated with any hair repair solution, had 62% of its water remaining in it. This Example demonstrates that the test composition made the hair of Tress 1 less porous and more hydrophobic, which resulted in faster hair drying.

Example 3: Retention of Hair Dye after Oxidative Hair Dyeing

Hair tresses were dyed using a conventional oxidative hair dye in the shade of red following the manufacturer's instructions. With Tress 1, 10 ml of the test composition was added to the hair dying paste. With Tress 2, no hair repair solution was added to the dying paste. After the hair was dyed and left to air dry, both hair tresses were washed by hand with equal amounts of a consumer shampoo product. The foam from each tress washing was retained. The foam samples were photographed, and analyzed by colorimetric software (Image Analysis Summarizer v0.76). The colorimetry results using the L*a*b system of the International Commission on Illumination are reported in Table 2.

In this system, larger L values indicate a lighter color intensity, whereas larger a values indicate a greater red color, and larger b values indicate a greater yellow color. The reported results are the median value of all pixels in the photos of the foam. Tress 1, which was treated with the test composition, had greater color fastness and less washout of color by shampoo. Washout foam from Tress 2, which was not treated with the test composition, was significantly darker (lower L value) and was more red and yellow (larger a and b values) indicating quantitatively that more red dye was being washed out by the shampoo.

TABLE 2

| Colorimetry of Washout Foam | Tress 1 | Tress 2 |
| --- | --- | --- |
| L value | 83 | 73 |
| a value | 1 | 3 |
| b value | 7 | 13 |

Example 4: Test Composition Applied to Hair and Exposed to UV Light

Three women, whose history of hair treatments including decades of chemical treatments such as bleaching, dying, and relaxing, and reported to have damaged hair, applied the composition of Table 3 to their hair, and left the composition on for a minimum of 3 hours. The three subjects exposed their hair to direct daylight for some or all the period of testing. All three subjects reported significant improvement in hair quality, less frizz, and easier ability to comb their hair.

TABLE 3

| Ingredient | Weight Percent |
| --- | --- |
| Water | 71.19% |
| *Aspergillus terreus* ferment dry solids and Arginine in a weight ratio of 6:2.5 | 7.31% |
| Cetearyl Alcohol | 5.0% |
| Behentrimonium Methosulfate | 3.0% |
| Stearamidopropyl Dimethylamine | 1.5% |

TABLE 3-continued

| Ingredient | Weight Percent |
| --- | --- |
| Sunflower Oil | 5.0% |
| Xanthan Gum | 1.0% |
| Propanediol | 1.0% |
| Phenoxyethanol | 1.0% |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions, methods, and processes without departing from the scope of the invention, it is intended that all matter contained in the above description shall be interpreted as illustrative and not in a limiting sense.

The invention claimed is:

1. A composition comprising a mixture of (a) an *Aspergillus terreus* fermentation product or a fraction or an isolate thereof and (b) a basic amino acid, wherein the weight ratio of the *Aspergillus terreus* fermentation product or the fraction or the isolate thereof to the basic amino acid is about 2:1 to about 10:1.

2. The composition of claim 1 wherein the composition has a concentration of the *Aspergillus terreus* fermentation product or the fraction or the isolate thereof that is from about 0.1 wt. % to about 20 wt. %.

3. The composition of claim 1 wherein the weight ratio of the *Aspergillus terreus* fermentation product or the fraction or the isolate thereof to the basic amino acid and/or the amino alcohol is from about 2:1 to about 5:1.

4. The composition of claim 1 wherein the *Aspergillus terreus* fermentation product or the fraction or the isolate thereof comprises an aqueous fermentation broth.

5. The composition of claim 1 wherein the *Aspergillus terreus* fermentation product or the fraction or the isolate thereof comprises a dried fermentation broth.

6. The composition of claim 1 wherein the composition has a concentration of the *Aspergillus terreus* fermentation product or the fraction or the isolate thereof that is about 20 wt. % or greater.

7. The composition of claim 1 wherein the basic amino acid comprises arginine and/or lysine.

8. The composition of claim 1 wherein the basic amino acid comprises arginine.

9. The composition of claim 1 wherein the composition further comprises an amino alcohol.

10. The composition of claim 9 wherein the amino alcohol comprises at least one alcohol selected from the group consisting of triethanolamine, diethanolamine, monoethanolamine, 2-amino-2-methyl-1-propanyl, and combinations thereof.

11. The composition of claim 1 wherein the composition further comprises at least one additive selected from the group consisting of surfactants, vitamins, natural extracts, preservatives, chelating agents, perfumes, preservatives, antioxidants, proteins, amino acids, humectants, fragrances, emollients, penetrants, thickeners, viscosity modifiers, hair fixatives, film formers, emulsifiers, opacifying agents, propellants, liquid vehicles, carriers, salts, pH adjusting agents, neutralizing agents, buffers, hair conditioning agents, antistatic agents, anti-frizz agents, anti-dandruff agents, and combinations thereof.

12. The composition of claim 1, further comprising an oxidizing agent or precursor thereof.

13. The composition of claim 12 wherein the oxidizing agent comprises at least one chemical selected from the group consisting of hydrogen peroxide, urea peroxide, alkali metal bromates, ferricyanides, peroxygenated salts, persulfates, and combinations thereof.

14. A method of treating hair fibers, the method comprising (a) contacting the hair fibers with the composition of claim 1; and (b) exposing the hair fibers treated with the composition to an oxidizing agent.

15. The method of claim 14 wherein the oxidizing agent comprises at least one chemical selected from the group consisting of hydrogen peroxide, urea peroxide, alkali metal bromates, ferricyanides, peroxygenated salts, persulfates, and combinations thereof.

16. The method of claim 14 wherein the oxidizing agent comprises UV light.

17. A method of treating hair fibers, the method comprising contacting the hair fibers with a hair treatment composition comprising an *Aspergillus terreus* fermentation product or a fraction or an isolate thereof, a basic amino acid, and an oxidizing agent, wherein the weight ratio of the *Aspergillus terreus* fermentation product or the fraction or the isolate thereof to the basic amino acid is about 2:1 to about 10:1.

18. The method of claim 17 wherein the oxidizing agent comprises at least one chemical selected from the group consisting of hydrogen peroxide, urea peroxide, alkali metal bromates, ferricyanides, peroxygenated salts, persulfates, and combinations thereof.

19. The method of claim 17 further comprising exposing the hair fibers to UV light.

20. A kit for treating hair comprising: a first container comprising the composition of claim 1; and a second container comprising a second composition comprising a hair chemical component comprising an oxidizing agent or precursor thereof.

21. A method of increasing hair color fastness, the method comprising contacting the hair fibers with a hair treatment composition comprising an *Aspergillus terreus* fermentation product or a fraction or an isolate thereof, a basic amino acid, a hair coloring dye, and an oxidizing agent, wherein the weight ratio of the *Aspergillus terreus* fermentation product or the fraction or the isolate thereof to the basic amino acid is about 2:1 to about 10:1.

22. A method of increasing hydrophobicity in hair fibers, the method comprising contacting the hair fibers with the composition of claim 1.

23. A hair conditioner or shampoo comprising the composition of claim 1.

* * * * *